United States Patent

Susawa et al.

[11] Patent Number: 5,591,222
[45] Date of Patent: Jan. 7, 1997

[54] METHOD OF MANUFACTURING A DEVICE TO DILATE DUCTS IN VIVO

[76] Inventors: Takashi Susawa, 13-2-309, Okubo-cho, Tanakakami, Sakyo-ku, Kyoto-shi, Kyoto-fu; Keiji Ioaki, 1-21, Wakakusa 2-chome, Kusatsu-shi, Shiga-ken; Hideo Tamai, 50-19, Miyake-cho, Moriyama-shi, Shiga-ken; Yoshihiko Shimizu, 39-676, Ogurayama, Kohata, Uji-shi, Kyoto-fu; Kaneto Shiraki; Akihiro Sato, both of 19, Kitaotsubo, Nishimachi 3-chome, Ayabe-shi, Kyoto-fu, all of Japan

[21] Appl. No.: 219,301

[22] Filed: Mar. 28, 1994

Related U.S. Application Data

[63] Continuation of Ser. No. 961,951, Oct. 16, 1992, abandoned.

[30] Foreign Application Priority Data

Oct. 18, 1991 [JP] Japan ...................................... 3-270810

[51] Int. Cl.$^6$ ................................ A61F 2/06; A61F 2/04; A61M 29/00
[52] U.S. Cl. .................... 623/1; 623/12; 606/195
[58] Field of Search ...................... 623/1, 11, 12; 600/36; 606/191–198, 151–158

[56] References Cited

U.S. PATENT DOCUMENTS

| | | | |
|---|---|---|---|
| 4,647,416 | 3/1987 | Seller, Jr. et al. | 623/1 |
| 4,655,771 | 4/1987 | Wallsten . | |
| 4,718,907 | 1/1988 | Karwoski et al. | 623/1 |
| 4,743,251 | 5/1988 | Barra . | |
| 4,870,966 | 10/1989 | Dellon et al. | 623/1 |
| 4,922,905 | 5/1990 | Strecker . | |
| 4,954,126 | 9/1990 | Wallsten . | |
| 5,061,281 | 10/1991 | Mares et al. . | |
| 5,064,435 | 11/1991 | Porter . | |
| 5,147,385 | 9/1992 | Beck et al. . | |
| 5,147,399 | 9/1992 | Dellon . | |
| 5,370,682 | 12/1994 | Schmitt et al. | 623/1 |

FOREIGN PATENT DOCUMENTS

| | | | |
|---|---|---|---|
| 0183372 | 6/1986 | European Pat. Off. | 623/1 |
| 9211824 | 7/1992 | WIPO . | |
| 92/15342 | 9/1992 | WIPO . | |

*Primary Examiner*—Debra S. Brittingham
*Attorney, Agent, or Firm*—Armstrong, Westerman, Hattori, McLeland, & Naughton

[57] ABSTRACT

A device for dilating ducts in vivo, comprising a balloon-tipped catheter to which a cylindrical stent prepared by knitting or braiding or weaving biodegradable fibers to easily reduce diameter of the cylinder to a predetermined value is attached in a compressed condition, method for preparing the device and a stent.

16 Claims, 4 Drawing Sheets

METHOD OF MANUFACTURING A DEVICE TO DILATE DUCTS IN VIVO

This application is a continuation of application Ser. No. 07/961,951 filed Oct. 16, 1992, now abandoned.

FIELD OF THE INVENTION

The present invention pertains to a device for dilating stenosed ducts in vivo, to the method for manufacturing such a device, and to the stent used for such a device.

BACKGROUND OF THE INVENTION

To dilate stenosed blood vessels, bile ducts, etc. in vivo, stent insertion into the stenosed area has been performed, as shown in the following examples:

(1) A balloon-tipped catheter is inserted into the stenosed area. The thus dilated area is kept dilated with a stent which is inserted through another balloon-tipped catheter (2-step method); and (2) Without a preliminary dilative step, a balloon-tipped catheter carrying a stent is inserted so that the area dilated by the balloon is kept dilated with the stent (1-step method).

For these conventional techniques, metallic stents (made of stainless steel, tantalum, etc.) have been used.

These metallic stents lack flexibility and are likely to cause stress to the ducts (e.g., blood vessels) in vivo. Because of these features, the use of conventional stents involves the following problems; (1) a possibility of causing inflammation and excessive hypertrophy of the stent-inserted area, leading to a recurrence of stenosis, and (2) permanent retention of the stent as foreign matter in vivo.

To avoid the stress caused by metallic stents, the use of stents made of resin has been considered. Stents made of resin cause less stress to the ducts in vivo. However, they are difficult to form into a desired shape. Furthermore, it is difficult to attach a resin stent to a balloon-catheter in a compressed condition, to expand the stent at the stenosed area and to keep it expanded. To overcome these shortcomings of resin stents, a proposal for stents made of shape-memory resin has been made (Japanese Patent Application Disclosure No. 1991-21262). If a stent made of shape-memory resin is used, it is possible to expand the stent within the stenosed area, but it is not always easy to control the degree of stent expansion precisely. Furthermore, such a stent also remains permanently in vivo, continuing to cause stress to the ducts in vivo (e.g., blood vessels), although the stress may not be severe.

The present invention is aimed at providing such a device for dilating ducts in vivo that involves no risk of causing restenosis and that does not remain in vivo indefinitely. The invention is additionally aimed at providing a method for manufacturing such a device.

SUMMARY OF THE INVENTION

Through studies to achieve the above-mentioned purposes, the inventors found that the risk of re-stenosis can be avoided by manufacturing a cylindrical stent prepared by knitting or weaving or braiding biodegradable fibers, which is to be inserted in a compressed condition. Based on this finding, this invention was completed.

The present invention provides a device for dilating ducts in vivo, which comprises a balloon-tipped catheter carrying a compressed stent prepared by knitting or weaving or braiding biodegradable fibers.

The present invention also pertains to a method for manufacturing a device for dilating ducts in vivo. With this method, a cylindrical stent prepared by knitting or weaving or braiding biodegradable fibers is compressed by being inserted through a smaller tube so that it can be attached to a balloon-tipped catheter.

The present invention additionally pertains to a method for manufacturing a device to dilate ducts in vivo. With this method, a cylindrical stent prepared by knitting or weaving or braiding biodegradable fibers is thermally set to a diameter that corresponds to the diameter of the inflated balloon. Subsequently, its diameter is reduced by being inserted into a tube with a smaller diameter. In this way, the stent is attached to a balloon-tipped catheter in a compression condition.

The present invention provides a stent which comprises biodegradable fibers and whose diameter is reduced by insertion of the stent into a smaller diameter tube.

DETAILED DESCRIPTION OF THE INVENTION

Figure 1:
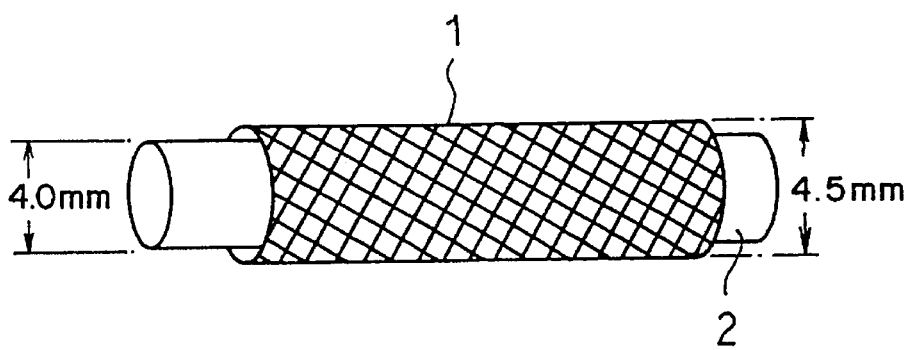
FIG. 1 is an illustration of the thermal treatment processes for the stent.

The term "ducts in vivo" in this document means ducts in vivo such as blood vessels, trachea, gastrointestinal tube, bile duct, urethra and ureter, which can develop stenosis.

The term "biodegradable fibers" indicates fibers that can be decomposed and eliminated by bodily process within about 1 to 24 months after insertion into the body of human and other mammals. They include, for example, fibers made of polylactic acid, polyglycolic acid, polyglactin (a copolymer of lactic acid and glycolic acid), polydioxanone, polyglyconate (a copolymer of trimethylene carbonate and glycolide), a copolymer of polyglycolic acid and $\epsilon$-caprolactone, and a copolymer of lactic acid and $\epsilon$-caprolactone. These fibers take the form of a filament thread of about 10 to about 1,000 µm in diameter so that a stent composed of these fibers may be firm enough and may easily maintain a cylindrical form. Among others, monofilament threads are most appropriate for this purpose. The mean molecular weight of biodegradable polymers is about 10,000 to about 800,000. The optimum biodegradable polymer depends on the stenosed ducts into which this stent is inserted. For a biodegradable stent to be used in stenosed blood vessels, polyglycolic acid is the optimum material.

In preparing a stent knitted with biodegradable fibers, it is desirable to use a plain stitch fabric so that the stent diameter can be easily reduced to a desired diameter.

In the invention, braided or woven fabric can be used in place of a knitted stent, however, a knitted stent is more preferable.

The stent of this invention is thermally set to a diameter larger than, equal to, or smaller than its original diameter and is subsequently compressed by being inserted into a tube, so that the stent may expand to a desired diameter within ducts in vivo. Thermal setting of the stent is performed by placing the stent in a mold with an appropriate diameter, so that the stent may retain the thermally set diameter after expansion in the stenosed region of the body. Thermal setting is performed at temperature higher than the glass transition point of the stent material and lower than the melting point of the stent material. For example, a stent made of polyglycolic acid is thermally treated at 105° C. for about 3 hours. The inner diameter of the expanded stent is about 3 to about 5 mm within the human coronary vessel and about 6 to about 10 mm within the human bile duct.

A compressed stent is obtained by inserting the thermally treated or untreated stent into a tube with a smaller diameter, that is, by folding the network loop of the stent and reducing the space between the fibers composing of the stent. This is done by pulling the stent tip through a smaller diameter tube, using a wire.

A compressed stent is provided either in the form of a stent pulled out of a smaller diameter tube or in the form of a stent inserted into a smaller diameter tube.

The tube through which the stent is passed is made of polytetrafluoroethylene (Teflon), polypropylene, etc. The desirable inner diameter of this tube is about 1.0 to about 5.0 mm, depending on the outer diameter of the balloon-tip catheter and the nature of the duct into which the catheter is to be inserted. To keep the stent compressed, it is recommended to thermally set the stent weakly. For example, a stent made of polyglycolic acid should be thermally set at 80° C. for about 5 minutes. Thermal setting for the compressed stent must not be stronger than thermal setting used during the manufacture of the stent before compression.

The present invention can be characterized by a combination of a thus prepared stent (cut into appropriate sizes) and a balloon-tipped catheter. A variety of conventionally known balloon-tipped catheters can be used for this combination.

Figure 6A:
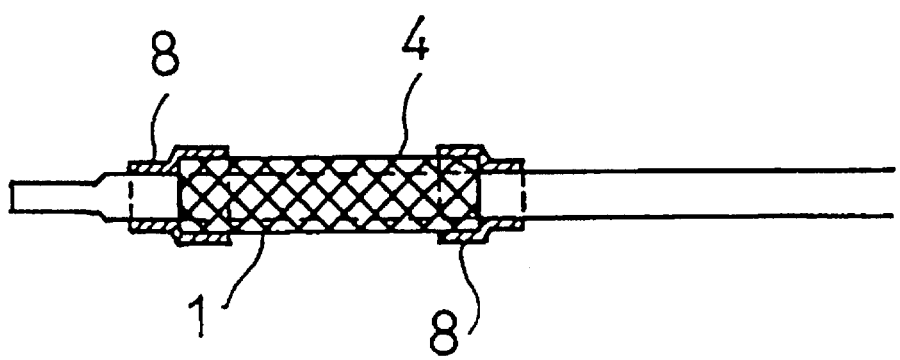
FIGS. 6(a) and 6(b) illustrate steps in an an example of the method for inserting the stent into a duct in vivo.
Figure 6B:
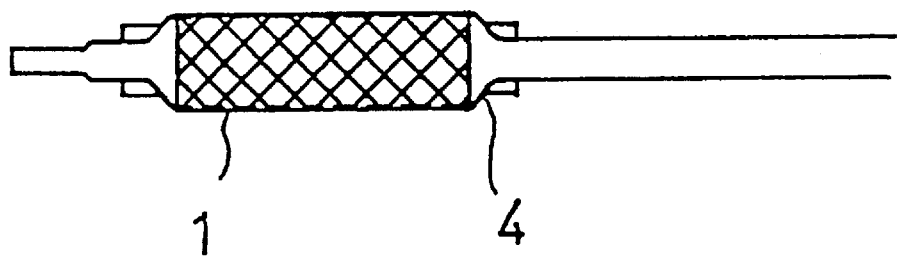
Figure 7A:
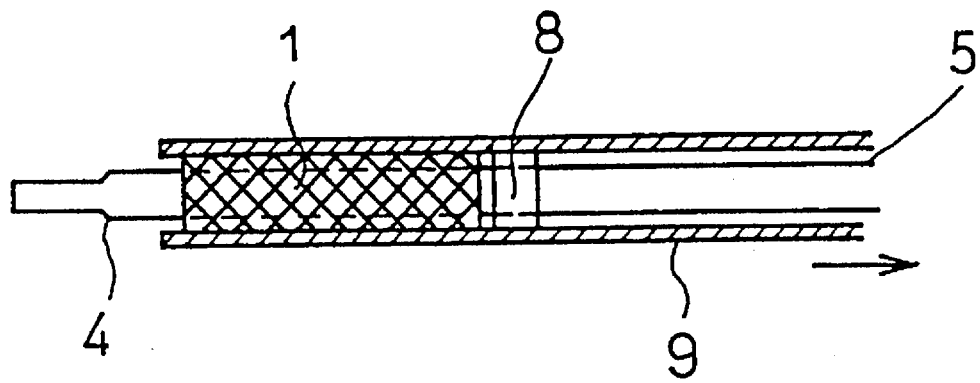
FIGS. 7(a), 7(b) and 7(c) illustrate steps in another example of the method for inserting the stent into a duct in vivo.
Figure 7B:
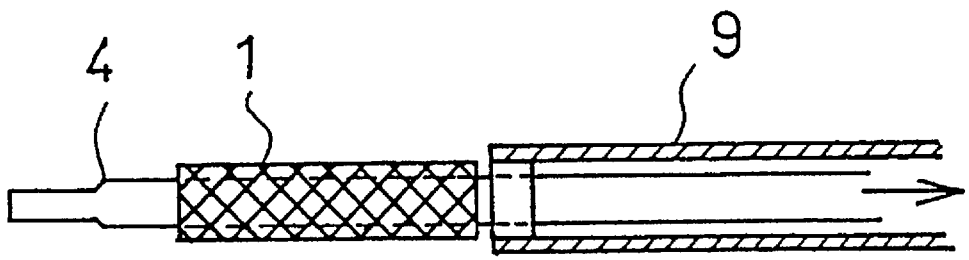
Figure 7C:
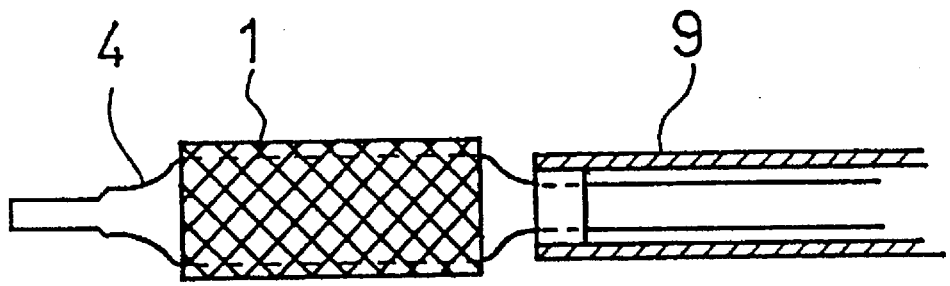

FIG. 6 shows an example of the procedure by which the compressed stent is inserted into stenosed duct of the human body. While holding the both ends of the stent (1) with silicone tubes (8), the stent is inserted into the duct. At the stenosed site of the duct, the balloon (4) is inflated, accompanied by expansion of the compressed stent (1). After the stent has expanded to its pre-compression diameter and is fixed within the duct, the balloon (4) is deflated and is withdrawn through the silicone tube (8). FIG. 7 shows another example. With this method, the stent (1) is attached to the catheter (5) and is held within a cover tube (9). At the stenosed site of the duct, the cover tube (9) is pulled back, and the stent (1) is exposed. Subsequently, the balloon (4) is inflated, followed by the same steps as in the first method for expanding the stent (1).

The stent of this invention is usually provided in a cylindrical form. The cross-section of the stent can have oval or other forms in addition to a circular form.

If a radiopaque substance, such as barium sulfate, is added to the resin composing the biodegradable fibers of this stent, the position and degradation of the stent in vivo can be checked by fluoroscopy.

The present invention has the following excellent effects.

(1) Since the stent comprises biodegradable fibers, the stent is decomposed and eliminated from the body after the stent has kept dilated the stenosed site of the duct for necessary periods. For this reason, it is unlikely that inflammation or excessive hypertrophy of the duct (which can lead to re-stenosis) is caused by prolonged physical stimulation with the stent. Thus, the stent of this invention provides a safe means of keeping the ducts dilated.

(2) Since the stent is compressed by being inserted into a tube with an appropriate inner diameter, the stent is contracted greatly in the direction of its diameter, without being simply extended in the axial direction. Thus, the stent diameter can be later increased within the duct in vivo, without being accompanied by contraction in the axial direction. The thus prepared stent can be easily expanded to a desired diameter following inflation of the balloon within the stenosed site of the duct in vivo.

(3) In a case where the stent of this invention is to be thermally set in an expanded condition, it is only necessary to match the diameter of the cylindrical stent to the minimal diameter which may be used. Strict accuracy in the stent size is not required. The thus prepared stent of a given diameter can be applied to various ducts in vivo.

EXAMPLE

Examples of application of this invention will be presented in more detail, using illustrations.

Example 1

As shown in FIG. 1, a plain stitch fabric stent (1), with a diameter of 4.5 mm, was knitted by using polyglycolic acid monofilaments (160 μm in diameter). This stent (1) was inserted into an inner tube (2), with an outer diameter of 4.0 mm, and was subsequently heated at 105° C. for 3 hours.

Figure 2:
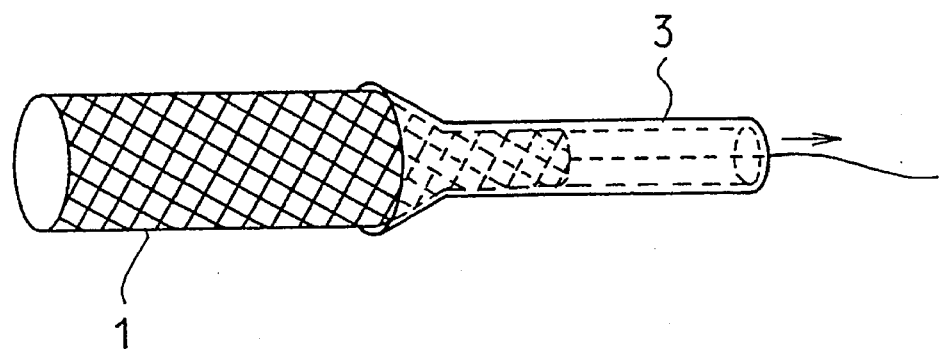
FIG. 2 shows stent contracting processes.
Figure 3:
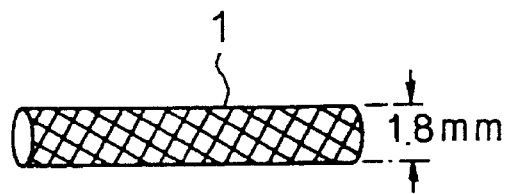
FIG. 3 shows a stent with a reduced diameter.
Figure 4:
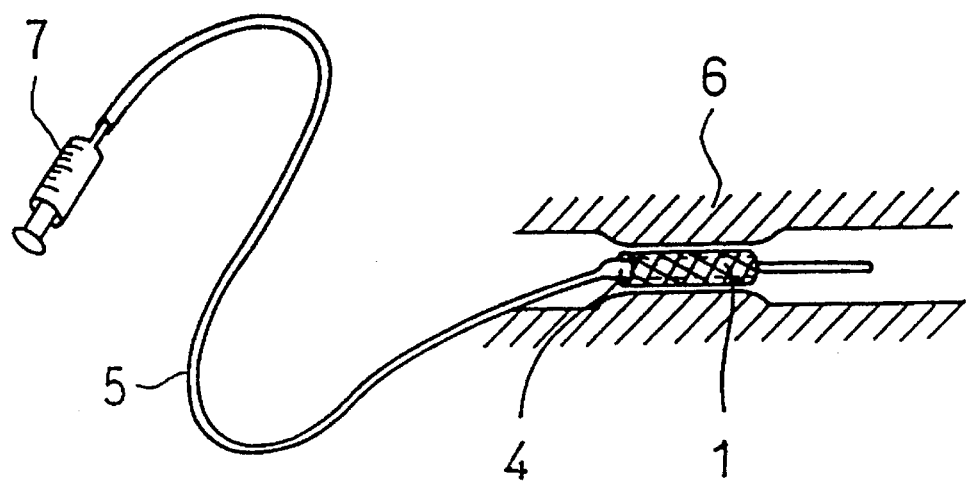
FIG. 4 is a schematic presentation of the procedure of inserting a stent into the stenosed site.
Figure 5:
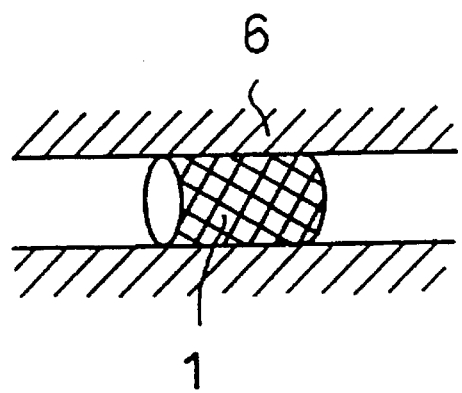
FIG. 5 shows an expanded stent within the stenosed site.

As shown in FIG. 2, the heat-treated stent (1) was thermally set at 80° C. for 5 minutes, while being passed through a Teflon tube with an inner diameter of 1.8 mm (3), using a wire. In this way, a stent compressed to an outer diameter of 1.8 mm was obtained (FIG. 3). This stent was tested in three adult mongrel dogs (body weight: 10–15 kg) under the same experimental condition. As shown in FIG. 4, the stent (1) was attached to a catheter (5) carrying a balloon (4). The catheter was inserted into the stenosed site of the coronary artery (6) of the three dogs. At the stenosed site, the balloon (4) was inflated with a compressor (7), followed by expansion of the stent (1) to an outer diameter of 4 mm. The balloon was then deflated and was withdrawn together with the catheter (5), leaving the stent (1) within the stenosed site (6). FIG. 5 schematically presents the stenosed coronary artery dilated by the stent (1).

Table 1 shows the results of pathological and angiographic examinations of the stenosed site after stent insertion.

TABLE 1

| Animal | Duration of stent's effect | Stent remained in place for | Inflammation/ Hypertrophy |
| --- | --- | --- | --- |
| 1 | 3 weeks | 3 months | absent |
| 2 | 4 weeks | 3 months | absent |
| 3 | 4 weeks | 3 months | absent |

Thus, the stent continued to keep the vessel dilated for 3–4 weeks, and it was absorbed into the body about 3 months after insertion. No animals showed inflammation or excessive hypertrophy of the stent-inserted region.

We claim:

1. A method for manufacturing a device for dilating ducts in vivo by application of pressure by a balloon-tipped catheter, comprising the steps of: providing a cylindrical stent prepared by forming biodegradable fibers by a procedure selected from the group consisting of knitting or braiding or weaving; thermally setting said stent to a diameter corresponding to a diameter of an inflated balloon of a balloon-tipped catheter, subsequently reducing the diameter of the stent in a compressed fashion to one permitting reception on the balloon of said balloon-tipped catheter when deflated by inserting the stent into a tube whose diameter is smaller than the diameter of the stent, thermally setting said stent at said compressed diameter, and attaching the compressed stent to the balloon-tipped catheter.

2. A method for making a device for dilating ducts in vivo, comprising the steps of:

providing a reduceable and expandable generally tubular stent formed of biodegradable fibers selected from the group consisting of knitted, braided and woven fibers and being of an initial length and an initial diameter, conducting a first thermal setting step by thermally setting said stent to a diameter different than said initial diameter, contracting said stent to reduce its diameter to one less than said initial diameter, and conducting a second thermal setting step by thermally setting said stent of reduced diameter at a temperature lower than that at which said first thermal setting step is conducted, whereby said thermally set reduced diameter stent is expandable from said reduced diameter by the application of a pressure from inside the stent.

3. The method of claim 2, wherein the first thermal setting step is conducted at a temperature between the glass transition point and the melting point of the biodegradable fibers.

4. The method of claim 2, wherein said step of contracting includes inserting said stent into and through a tube having at least a portion with an inner diameter substantially smaller than the initial diameter of the stent.

5. The method of claim 4, wherein said step of inserting includes pulling the stent through the tube by a pulling means.

6. The method of claim 4, wherein said step of inserting includes providing the pulling means as a wire operatively connected to said stent.

7. The method of claim 4, wherein said step of contracting includes providing the tube to be made with polytetrafluoroethylene (Teflon).

8. The method of claim 4, wherein said step of contracting includes providing the inner diameter of the portion of the tube that is substantially smaller than the initial diameter of the stent to be about 1.0 to 5.0 mm.

9. The method of claim 2, further including a step of expanding the stent from the reduced diameter to the initial diameter by applying a pressure inside the stent.

10. The method of claim 2, wherein said step of expanding includes providing a catheter having an expandable balloon which is inserted within the stent and inflated so as to apply the pressure inside the stent.

11. The method of claim 2, wherein said step of providing a generally tubular stent includes providing the stent with a generally circular cross section.

12. The method of claim 2, wherein said step of providing a generally tubular stent having reduceable and expandable biodegradable fibers includes providing a plain stitch fabric stent.

13. The method of claim 2, wherein said step of providing a generally tubular stent having reduceable and expandable biodegradable fibers includes providing biodegradable fibers made of biodegradable polymers selected from the group consisting of polylactic acid, polyglycolic acid, polyglactin (a copolymer of lactic acid and glycolic acid), polydioxanon, polyglyconate (a copolymer of trimethylene carbonate and glycolide), a copolymer of polyglycolic acid and $\epsilon$-caprolactone, and a copolymer of lactic acid and $\epsilon$-caprolactone.

14. The method of claim 2, wherein said biodegradable fibers are provided as knitted.

15. The method of claim 2, wherein said biodegradable fibers are provided as monofilament having a diameter of about 10 to about 1,000 μm.

16. The method of claim 2, wherein an initial inner diameter of the expanded stent is about 3 to about 10 mm.

* * * * *

UNITED STATES PATENT AND TRADEMARK OFFICE
CERTIFICATE OF CORRECTION

PATENT NO.  : 5,591,222
DATED       : January 7, 1997
INVENTOR(S) : SUSAWA et al.

It is certified that error appears in the above-identified patent and that said Letters Patent is hereby corrected as shown below:

Item [76], line 3, please change the spelling of the second inventor's last name from "Ioaki" to --Igaki--.

Signed and Sealed this

Thirtieth Day of December, 1997

*Attest:*

BRUCE LEHMAN

*Attesting Officer*     *Commissioner of Patents and Trademarks*